United States Patent [19]

Young

[11] 4,447,530
[45] * May 8, 1984

[54] BIOCONVERSION OF INDUSTRIAL CELLULOSIC PULP MATERIALS TO PROTEIN-ENRICHED PRODUCT

[76] Inventor: Murray M. Young, 63-50 Bluesprings Dr., Waterloo, Ontario, Canada, N2J 4M1

[*] Notice: The portion of the term of this patent subsequent to Apr. 12, 2000 has been disclaimed.

[21] Appl. No.: 445,487

[22] Filed: Nov. 30, 1982

Related U.S. Application Data

[63] Continuation of Ser. No. 240,329, Mar. 4, 1981, Pat. No. 4,379,844, which is a continuation-in-part of Ser. No. 3,998, Jan. 17, 1979, abandoned.

[51] Int. Cl.$^3$ ............................................. C12P 21/00
[52] U.S. Cl. ..................................... 435/68; 435/252; 435/911; 426/52; 426/53; 426/807
[58] Field of Search ................. 426/49, 52, 53, 55–56, 426/623, 630, 636, 807; 435/251, 911, 252–254, 68, 804, 822

[56] References Cited

U.S. PATENT DOCUMENTS

| | | | |
|---|---|---|---|
| 3,761,355 | 9/1973 | Callihan et al. | 435/822 X |
| 3,937,845 | 2/1976 | Han et al. | 426/53 |
| 4,062,727 | 12/1977 | Srinivasan et al. | 435/804 X |
| 4,379,844 | 4/1983 | Young | 435/251 |

OTHER PUBLICATIONS

Moo Young et al., "Single Cell Protein from Various Chemical Treated Wood Substrates Using Chaetomium Cellulolyticum", Biotech. & Bioeng., 1978, (20), pp. 107–118.

Moo Young et al., Single Cell Protein Production of Chaetomium Cellulolyticum–a New Thermotolerant Cellulolytic Fungus, Chemical Abstracts, vol. 86, Abs. No. 153935j.

*Primary Examiner*—R. B. Penland
*Attorney, Agent, or Firm*—Sim & McBurney

[57] ABSTRACT

An industrial cellulosic pulp material, such as wood pulp and paper stock, pulp sludges resulting from the manufacture of paper, coffee and sugar and starch-rich cellulosic materials, such as, bananas and root crops, is converted into a protein-enriched producing having significant amounts of microbial biomass in the form of the fungus, *Chaetomium cellulolyticum*.

4 Claims, No Drawings

BIOCONVERSION OF INDUSTRIAL CELLULOSIC PULP MATERIALS TO PROTEIN-ENRICHED PRODUCT

REFERENCE TO RELATED APPLICATION

This application is a continuation of copending application Ser. No. 240,329 filed Mar. 4, 1981 (now U.S. Pat. No. 4,379,844), which itself is a continuation-in-part of Ser. No. 003,998 filed Jan. 17, 1979 (now abandoned).

FIELD OF INVENTION

The present invention relates to the conversion of cellulosic materials by a fermentation process into products which contain microbial biomass, such products being useful as human or animal food for their protein and other nutritive values. In the following description concentrations of substances are expressed as W/V (for weight per unit volume of total mixture), as V/V (for volume per unit volume of total mixture), as W/W (for weight per unit weight of total mixture), or as DM (for weight per unit weight of total mixture on a dry matter basis).

BACKGROUND TO THE INVENTION

Vast quantities of cellulosic materials occur universally as surplus and waste residues of industrial processing and other operations. They occur in various processed forms, such as, pulp sludges from the manufacture of paper, commonly known as clarifier sludge, coffee, commonly known as coffee grounds, and cane sugar, commonly known as bagasse pith. Basically, these materials contain cellulose, usually in combination with significant amounts of hemicellulose and smaller amounts of lignin. Because of their carbohydrate content, these materials represent potentially valuable biorenewable resources for fermentation processes in the production of edible microbial protein.

Various known processes have been proposed or used to convert cellulosic materials into products which are purported to be suitable, as substitute for hay and similar forages, for metabolisable carbohydrate energy in ruminant feeds. These processes use physical and/or chemical changes of the materials merely to enhance their digestibility; none of the original cellulosic material is converted into protein.

Various known processes have also been proposed or used to convert cellulosic materials into products which are purported to be suitable, as substitutes for soymeal and similar protein-rich substances, for animal feed protein rations. Of these, two basic types of fermentation processes are known. In the first method, yeasts are cultivated on liquid sugar solutions which are produced by chemical hydrolysis of the hemicellulose and/or cellulose components of the cellulosic material. In the second method, cellulolytic bacteria are cultivated on the solid cellulose and/or hemicellulose components of the cellulosic material.

In the above prior art processes, one or more of the following undesirable features are found: (1) the processing costs are high, because conversion rates are low and/or chemical pretreatment, usually under severe conditions, of the material is required, (2) the product is not suitable as animal feed, because it is too toxic and/or too indigestible, (3) the product is not suitable as animal feed protein ration, because its protein content is too low and/or its protein quality is too poor.

In a publication by the inventor and his co-workers entitled "SCP Production by *Chaetomium cellulolyticum*, a new Thermotolerant Cellulolyticum Fungus", Biotechnology and Bioengineering, vol. XIX, pages 527 to 538 (1977), it is disclosed that *Chaetomium cellulolyticum* showed 50 to 100% faster growth rates and over 80% more final biomass-protein formation than *Trichoderma viride* when cultivated on highly purified cellulose as the sole carbon source in the fermentation media.

This article also discloses that for other forms of cellulose (namely, sawdust) extensive pretreatment is required to render the material susceptible to use for fermentation.

SUMMARY OF INVENTION

The present invention obviates the prior art problems by providing a novel fermentation process for economically treating an industrial cellulosic material, which may be a wood product, such as, wood pulp or paper stock, a waste material such as sludge, from the making of paper, coffee and sugar, or cellulosic-starchy materials, such as, bananas, potatos, yams and cassava. The cellulosic material is not subjected to pretreatment other than to sterilize the same, if not already sterile, and is supplemented with non-carbon nutrient chemical additives, the cellulosic material providing the carbon source. The cellulosic material, which is in the solid phase, is converted by aerobic fermentation into a protein-enriched product containing significant amounts of microbial biomass in the form of the fungus, *Chaetomium cellulolyticum* (ATCC 32319), the product being suitably safe, digestible and nutritious for animal and human consumption.

GENERAL DESCRIPTION OF INVENTION

Raw Material

The present invention is concerned with the conversion of a cellulosic carbohydrate material into a microbial biomass product by fermentation. The term "cellulosic material" as used herein signifies an industrial cellulosic pulp material containing at least 10% DM cellulose, including wood pulp and paper stock, and cellulosic waste materials, such as, pulp-mill sludge, for example from a Kraft-type pulp mill, coffee bean residues and sugar cane fibre residue.

While the invention is particularly concerned with utilization of such predominantly cellulosic carbohydrates, the invention is also concerned with the conversion of cellulosic carbohydrate materials which are associated with substantial quantities of non-cellulosic carbohydrates, such as, starches, into the microbial biomass product. Cellulosic carbohydrate materials of this type include bananas and root crops, for example, potato, yam and cassava.

The ability to use normally waste materials to form nutritionally useful protein-enriched products is a significant environmental pollution control factor.

The Process

The process of the present invention consists essentially of two steps: (1) aerobic fermentation of a sterile mixture of the ellulosic material and a nutrient supplement solution, and (2) separation of the solids from the fermented mixture. Optionally, the separated solid product may be dried.

The cellulosic material generally is particulated prior to commencement of the process. If used in granular form, the particles may have an average particle size in the range of up to about 5 mm mesh. If used in fibrous forms, fibre sizes up to 20 mm in length may be used.

The particulated cellulosic material is mixed with nutrient supplements to provide the essential non-carbon nutrients which are lacking in the cellulosic material. The cellulosic material provides the carbon source for growth of the microorganism. As is well known in the art, certain essential elements are required to be present in a fermentation medium to achieve proper microbial growth. As used herein, the term "non-carbon nutrients" refers to the conventional nutrients other than carbon. The fermentation medium is supplemented from an external source of non-carbon nutrients to provide an overall composition of mixture which conforms to conventional guidelines for fermentation medium formulations. Typically, the major elements as carbon, nitrogen, phosphorus and potassium follow the ratios of C:N:P:K=100:10:1:1 by weight.

The fermentation medium, consisting of the mixture of cellulosic material and the nutrient supplement solution, is sterilized, if required, by any conventional procedure, for example, by the heating for a period using live steam or indirect heat. The cellulosic material is not subjected to any pretreatment process in this invention, in contrast to the Moo-Young et al article mentioned above. The nature of the industrial cellulosic pulp material which is fermented in accordance with this invention permits fermentation to occur without the necessity for the severe pretreatment operations of the prior art.

The consistency of the slurry is preserved at a value suitable for submerged fermentation, such as, up to about 3% W/V solids. The fermentation may, however, be effected at any desired concentration up to about 30% W/W allowable by standard solid-state fermentation techniques, for example, at an overall solids concentration of generally about 15 to about 30% W/W of the mixture.

The nutrient supplement solution may be provided from any convenient source, such as, a synthetic mixture of chemicals containing the non-carbon elements required for supplementation, for example, a fertilizer blend. The nutrient supplement solution may also be provided by an animal manure, such as, cattle or swine manure. The animal manure may be anaerobically pre-digested, if desired, to coproduce methane as a valuable fuel by-product.

The fermentation medium is adjusted, if necessary, to a pH in the range of about 5 to about 8, particularly about 5 to about 7, and inoculated with the fungus, *Chaetomium cellulolyticum*. Fermentation is effected at a temperature of about 30° to about 40° C., typically around 37° C., using sterile air, typically supplied at a flow rate of 1 to 2 volumes of air per unit volume of medium per minute.

During the fermentation, the fungus uses the raw materials to reproduce itself and generate cellulase-enzymes, which hydrolyse the carbohydrate contents to fermentable substances and also soften and thereby improve the digestibility of any solid cellulosic material which remains unutilized. The fermentation is continued until the desired fungus growth has been effected, for example, for about 12 to about 24 hours, if conducted batchwise. In continuous operations, an average residence time of the fermentation medium is typically 4 to 8 hours for adequate growth.

Following completion of the fermentation, the solid phase is separated from the liquid phase. The separated solid phase may be used as such, or the separated solid phase may be dried to a low moisture content, generally below about 10% W/W, typically about 8% W/W. The liquid phase may be reused, if desired.

The solid phase product contains *Chaetomium cellulolyticum* in variable quantities, depending on the extent and conditions of the fermentation. The product contains at least about 5% DM of biomass, usually from about 20 to about 80% DM. The remainder of the solid phase is unfermented cellulosic material.

*Chaetomium cellulolyticum* is a newly isolated fungus freely available from the American Type Culture Collection (ATCC No. 32319) and has the following capabilities: (1) utilization of a variety of cellulosic as well as non-cellulosic carbohydrate materials as carbon nutrient for growth, (2) utilization of a variety of synthetic as well as non-synthetic mixtures as non-carbon nutrient supplement for growth, (3) growth over a range of pH of about 5 to 8, the optimal being about pH 5 for insoluble cellulose and about pH 7 for solubilized hemicellulose, and (4) growth over a range of temperature of about 30° C. to 45° C., the optimal being about 37° C.

The average composition of the fungus is as follows (%DM basis): 45% crude protein, 40% carbohydrates, 10% fats, 5% vitamins, minerals, etc. The following Table shows that the amino acid profile of the protein component of the fungus is nutritionally sound and is comparable with fodder yeast (*C. utilis*), soymeal protein and the UN-FAO reference protein for human nutrition.

TABLE

| Amino Acid | C. cellulolyticum | C. utilis | Soy-meal | FAO reference |
|---|---|---|---|---|
| Threonine | 6.1 | 5.5 | 4.0 | 2.8 |
| Valine | 5.8 | 6.3 | 5.0 | 4.2 |
| Cystine | 0.3 | 0.7 | 1.4 | 2.0 |
| Methionine | 2.3 | 1.2 | 1.4 | 2.2 |
| Isoleucine | 4.7 | 5.3 | 5.4 | 4.2 |
| Leucine | 7.5 | 7.0 | 7.7 | 4.8 |
| Tyrosine | 3.3 | 3.3 | 2.7 | 2.8 |
| Phenylalamine | 3.8 | 4.3 | 5.1 | 2.8 |
| Lysine | 6.8 | 6.7 | 6.5 | 4.2 |

The product of the process of the invention has been found by in-vivo and in-vitro feeding trials to be suitable as animal feed ingredient.

EXAMPLES

The examples given below further illustrate the present invention. It should be understood that the invention is not limited to these particular examples.

Unless otherwise specified, the source of nutrient supplement to provide essential elements other than carbon for the fungal growth referred to in the examples below are as follows:

(1) Solution A. A synthetic mixture containing in one liter of aqueous solution 2 g $KH_2PO_4$, 1.4 g $(NH_4)_2SO_4$, 0.3 g urea, 0.3 g $MgSO_4.7H_2O$, 0.3 g $CaCl_2$, 5 mg $FeSO_4.7H_2O$, 1.6 mg $MnSO_4.H_2O$, 1.4 mg $ZnSO_4.7H_2O$, 2 mg $CoCl_2$.

(2) Solution B. A non-synthetic mixture of swine manure (feces plus urine) diluted with water to contain about 0.05% W/V inherent nitrogen, the other naturally-occurring ingredients being reduced accordingly, and enriched with 0.05% W/V added nitrogen as (NH$_4$)$_2$SO$_4$.

The inoculum for the fermentations referred to in the examples below was prepared as follows. The fungus *Chaetomium cellulolyticum* is grown in serial transfers from a glucose-based fermentation medium to the actual cellulosic-based medium, using well-known standard techniques. Visible microbial growth was allowed to develop for one day after which it was removed and disrupted under aseptic conditions in a blender resulting in a suspension of microbial pieces, typically containing about 5% W/V solids. A small amount of this suspension, typically 5% V/V of the medium to be fermented, constitutes the inoculum.

EXAMPLE 1

A fermentation medium consisting of 1% W/V of a wood pulp (delignified spruce wood pulp having average fibre lengths of about 1 cm) in a solution containing 50% V/V tap water and 50% V/V Solution A, was sterilized with live steam. After cooling the prepared medium to 37° C. and adjusting the pH to 5 with 2N H$_2$SO$_4$ solution, it was seeded with a 5% V/V inoculum and fermented at 37° C. with sterile air using standard submerged fermentation shake-flask techniques.

After a growth period of 20 hours, the fermented solids were removed by filtration and dried in an oven overnight at about 80° C. to a moisture content of about 8% CM. It was found that the microbial biomass content of the solids in the original fermentation medium increased from zero to 91% DM (corresponding to a crude protein content of 41% DM) the balance being unfermented cellulosic material. In standard in-vivo feeding trials using rats, the product was found to be favourably comparable to casein for up to 40% DM protein replacements of casein which was used in the "control" diets, with respect to non-toxicity, non-teratogenecity, digestibility and protein nutritional value.

EXAMPLE 2

A fermentation medium was prepared and fermented as described in Example 1 for a growth period of 18 hours using a ground sample of Kraft-type pulp-mill sludge (average particle size of about 1 mm mesh size) as the cellulosic material.

The dried product contained 60% DM of the microbial biomass and 40% DM unfermented cellulosic material and had an in-vitro digestibility, as determined by standard in-vitro feeding trials using cattle rumen fluid, of 45% DM. By way of comparison, the value for normal forage-quality hay is about 50% DM.

EXAMPLE 3

The experiment of Example 1 was repeated, except that Solution B was used as the nutrient supplement in place of Solution A.

Following a growth period of 20 hours and drying of separated solid material, the microbial biomass content of the dried product was 49% DM, the balance being admixed unfermented cellulosic material. In standard in-vivo feeding trials with rats, the product was comparable to casein for up to 20% DM protein replacements in the "control" diets.

EXAMPLE 4

The experiment of Example 1 was repeated, except that the cellulosic material used was a sample of newsprint paper shredded into 2 cm strips.

Following a growth period of 20 hours and drying of the separated solids, the microbial biomass content of the product was found to be 20% DM.

EXAMPLE 5

The experiment of Example 1 was repeated, except that the cellulosic material used was a sample of coffee grounds waste residue milled to 1 mm mesh size.

After a growth period of 15 hours, the microbial biomass content of the dried product was found to be 38% DM.

EXAMPLE 6

The experiment of Example 4 was repeated, except that the cellulosic material used was a sample of sugarcane bagasse pith milled to pass 1 mm mesh size.

After a growth period of 12 hours, the microbial biomass content of the product was found to be 16%.

EXAMPLE 7

The experiment of Example 1 was repeated except that the cellulosic material was replaced by a sample of "Irish" potato remnants (including skin) blended into the fermentation medium.

After a growth period of 24 hours, the microbial biomass content of the product was found to be 99.8% DM.

EXAMPLE 8

(a) A series of fermentation experiments was conducted using three different organisms, namely, *Chaetomium cellulolyticum* (Organism A), *Trichoderma viride* (Organism B) and *Phanerochaete chrysosporium* (Organism C). The latter two organisms were chosen since they are purported to be the most efficient converters of cellulosic solid materials into microbial protein.

In the experiments, Kraft pulp mill clarifier sludge of about 1 mm mesh size average particle size was used as the cellulosic material and Solution A was used to provide the non-carbon nutrients. Three batches of fermentation medium were inoculated with the organism and fermented using standard aerated shake-flask techniques at 37° C. and an initial pH of 5.

All three organisms grew according to the usual exponential and growth-saturated patterns and the rates and extents of microbial biomass protein formation were determined. The results are reproduced in the following Table I:

TABLE I

| Organism | Protein Productivity Relative to Organism A (%) | Maximum Protein Production Relative to Organism A (%) |
|---|---|---|
| A | 100 | 100 |
| B | 55 | 51 |
| C | 46 | 19 |

The results of the above Table I show that *Chaetomium cellulolyticum* is significantly more efficient than the other two organisms, in terms both of protein productivity and maximum protein production.

(b) A further set of experiments was conducted in which 0.1% W/V yeast extract was added to Solution A and the following conditions of temperatures and pH were used for the various organisms:

| Organism A | 37° C., pH 5 |
| Organism B | 30° C., pH 5 |
| Organism C | 37° C., pH 4.5 |

All three organisms grew according to the usual exponential and growth-saturated patterns and the results for the rates and extents of microbial biomass protein production are given in Table II:

TABLE II

| Organism | Protein Productivity Relative to Organism A (%) | Maximum Protein Production Relative to Organism A (%) |
| --- | --- | --- |
| A | 100 | 100 |
| B | 31 | 88 |
| C | 26 | 53 |

The results of the above Table II show that, even in the presence of an expensive medium additive which purportedly provides the "best" culture conditions for Organisms B and C, *Chaetomium cellulolyticum* significantly excelled in terms of the rate and extent of protein product formation.

SUMMARY

In summary of this disclosure, the present invention, therefore, provides a procedure for converting certain cellulosic materials into products which contain a fungal microbial biomass, useful as protein-enriched animal or human foodstuff. Modifications are possible within the scope of the invention.

What I claim is:

1. A process for the formation of proteinaceous material, which consists of:
   (a) aerobically fermenting a sterile mixture of a cellulose-starchy material in divided form selected from the group consisting of banana, potato, yam and cassava and a solution of non-carbon nutrient supplement in a culture of the fungus, *Chaetomium cellulolyticum*, at a pH of about 5 to about 7 and at a temperature of about 30° to about 45° C. for a time sufficient to grow the fungus and provide a solid mass consisting of about 20 to about 80% DM of the fungus and the balance of unfermented cellulose-starchy material, and
   (b) separating the resulting solid mass from the fermentation medium.

2. The process of claim 1 wherein said non-carbon fermentation nutrient chemical solution is a synthetic mixture of nutrient element-containing chemicals.

3. The process of claim 1 wherein said non-carbon fermentation nutrient chemical solution is formed by anaerobically digesting animal manure.

4. The process of claim 3, wherein said animal manure is swine manure.

* * * * *